(12) United States Patent
Käpplein et al.

(10) Patent No.: US 7,713,476 B2
(45) Date of Patent: May 11, 2010

(54) APPARATUS FOR PREFERABLY AUTOMATIC HANDLING AND/OR PROCESSING OF OBJECTS

(75) Inventors: Andreas Käpplein, St. Leon-Rot (DE); Robert Gropp, Schifferstadt (DE); Peter Scheck, Rauenberg (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 2669 days.

(21) Appl. No.: 09/793,199

(22) Filed: Feb. 26, 2001

(65) Prior Publication Data

US 2002/0018733 A1 Feb. 14, 2002

(30) Foreign Application Priority Data

Mar. 3, 2000 (DE) .............................. 100 10 140

(51) Int. Cl.
*G01N 33/48* (2006.01)
(52) U.S. Cl. ................ 422/64; 422/63; 422/82.05; 436/43; 436/46; 436/49
(58) Field of Classification Search .............. 422/63, 422/64, 82.05; 436/43, 46, 49; 382/128
See application file for complete search history.

(56) References Cited

U.S. PATENT DOCUMENTS

| | | | |
|---|---|---|---|
| 3,195,502 A | | 7/1965 | Levy |
| 4,911,915 A | | 3/1990 | Fredenburgh |
| 5,190,428 A | * | 3/1993 | Bryant et al. .............. 414/403 |
| 5,582,796 A | * | 12/1996 | Carey et al. ................. 422/65 |
| 6,366,206 B1 | * | 4/2002 | Ishikawa et al. .......... 340/573.1 |
| 6,418,236 B1 | * | 7/2002 | Ellis et al. .................. 382/128 |

FOREIGN PATENT DOCUMENTS

| | | |
|---|---|---|
| DE | 19621179 A1 | 11/1997 |
| DE | 19802462 A1 | 8/1999 |
| DE | 29921159 U1 | 3/2000 |
| EP | 0 849 582 A2 | 6/1998 |

* cited by examiner

*Primary Examiner*—Lyle A Alexander
(74) *Attorney, Agent, or Firm*—Hodgson Russ LLP

(57) ABSTRACT

An apparatus for preferably automatic handling and/or processing of objects (1), in particular in the field of medical technology, having at least one processing station (3) and one object carrier (2) for bringing the object (1) to the processing station (3), optionally through the processing station (3), and away from the processing station (3), is characterized in that the object carrier (2) has a code; that data concerning the object (1) and/or the handling or processing of the object (1) can be assigned to the code; and that the data can be read or retrieved by way of the code.

1 Claim, 6 Drawing Sheets

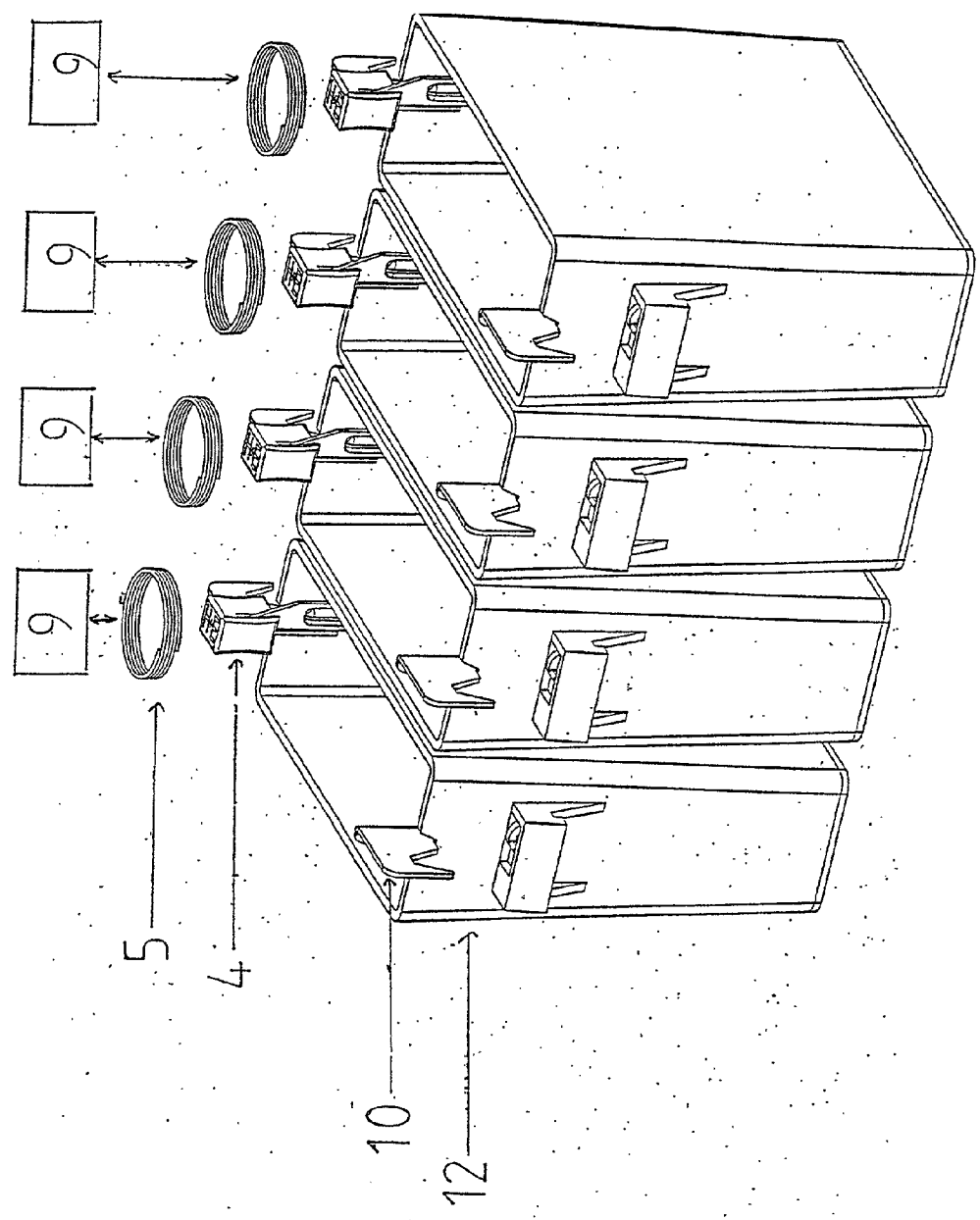

APPARATUS FOR PREFERABLY AUTOMATIC HANDLING AND/OR PROCESSING OF OBJECTS

CROSS-REFERENCE TO RELATED APPLICATIONS

This invention claims priority of a German patent application DE 100 10 140.2-52 filed Mar. 3, 2000 which is incorporated by reference herein.

FIELD OF THE INVENTION

The invention concerns an apparatus for preferably automatic handling and/or processing of objects, in particular in the field of medical technology, having at least one processing station and one object carrier for bringing the object to the processing station, optionally through the processing station, and away from the processing station.

BACKGROUND OF THE INVENTION

Apparatuses of the generic type are known from a wide variety of fields. Very generally, they are apparatuses used for handling and/or processing objects of any kind. The objects are delivered either to a single processing station or to multiple processing stations, usually in a predefined sequence; processed therein; and then lastly transported away from the processing station, in which context different groups of processing stations can be arranged one behind another.

Reference is made, purely by way of example, to EP 0 849 582 A2. This document discloses an apparatus for treating objects, in particular cytological or histological specimens, in which cytological or histological specimens are delivered by way of an object carrier or basket to an automatic stainer, the automatic stainer comprising multiple processing stations. Once the object has been delivered to the automatic stainer, identification of the object or indeed of multiple objects within the automatic stainer is no longer possible. Simultaneous processing of different specimens is therefore not possible with the known apparatus, since there is a risk of mixing up different specimens. With the known apparatus is also not possible simultaneously to run different staining programs with identical or different specimens, since no distinction can be made among the various specimens that are to be differently processed or stained.

SUMMARY OF THE INVENTION

It is therefore the object of the present invention to configure and develop an apparatus for preferably automatic handling and/or processing of objects, in particular in the field of medical technology, in such a way that fully automatic operation is possible with unequivocal identification of the objects to be handled or treated. In addition, it should be possible to perform automatic program assignment to the respective objects.

The aforesaid object is achieved by way of the features of Claim 1. According to the latter, an apparatus of the generic type for preferably automatic handling and/or processing of objects, in particular in the field of medical technology, is characterized in that the object carrier has a code; that data concerning the object and/or the handling or processing of the object can be assigned to the code; and that the data can be read or retrieved by way of the code.

What has been recognized according to the present invention is that automatic program execution is possible only if the objects to be handled and/or processed can be unequivocally identified. For that purpose, the object carrier has a code assigned to it in unequivocal fashion; that code can by all means also be assigned to the object itself. In the case of histological or cytological specimens, however, it is advisable to assign the code to the object carrier, so that the object present thereon or therein is unequivocally identifiable by way of the code applied to the object carrier.

Further according to the present invention, data concerning the object and/or concerning the handling or processing of the object can be assigned to the code. In other words, the entire processing program can be assigned by way of the code to the object carrier and thus to the object, so that—also by way of the code—the entire program sequence is controllable. For that purpose, the data can be read or retrieved by way of the code, so that the position and status of the object can be ascertained or checked at any phase of processing. The prerequisite for automatic program execution with unequivocal identification of the object being processed or treated is created.

Specifically with regard to multi-stage processing, it is advantageous if multiple processing stations are arranged functionally and/or physically directly or indirectly after one another. In the context of such a functional concatenation of different processing stations, it is particularly important that the objects be unequivocally detectable at each processing station, namely by way of the code assigned to the object carrier and thus to the object.

The code assigned to the object carrier and thus to the object could be embodied as a mechanical code which in turn can be mechanically scanned and/or detected by way of a photoelectric barrier or the like. Upon passing through a processing station, that code, for example a lug mounted on the object carrier, could trigger a mechanically actuable proximity switch so that the presence of the object is recognized.

It is also possible for the code assigned to the object by way of its object carrier to be embodied as a barcode that is optically detectable at the respective processing stations or elsewhere. Ultimately the barcode is read by way of a reader wand or a reading unit arranged in stationary fashion, thus again making possible unequivocal identification of the object.

In very particularly advantageous fashion, the code is stored in an electrical, electromagnetic, or optical storage medium associated with the object carrier. In accordance with what has been stated above, the code can be read out from the storage medium so that in this respect as well, unequivocal identification of the object by way of the code is possible. Concretely, the object carrier can have a transmitter unit and optionally also a receiver unit; in very particularly advantageous fashion, the transmitter unit and optionally receiver unit associated with the object carrier can be a transponder. Any heretofore known embodiments of commercially available transponders can be used in this context; what is essential is that the transponder be activatable at definable locations, for example at the respective processing stations, in order to emit a signal or emit the code. Activation is usually accomplished by way of an activation or excitation coil, which accomplishes both activation of the transponder to emit a signal and signal transfer.

In the context of an advantageous exemplary embodiment, several or all processing stations can have associated with them an excitation coil, movable in the region of the processing stations, for activation of the transponder. It is also conceivable for each processing station to have associated with it a separate excitation coil that is then arranged in stationary fashion.

The transponder could be embodied as a read-only transponder or as a combined write/read transponder. In that context, it would be conceivable for the transponder to emit predefined code data or to be loadable with code data that it can emit after corresponding loading and after activation. As already mentioned above, all variants of commercially available transponders can be used in the context of the present invention.

In terms of design, it is very particularly simple if the transponder is immovably joined to the object carrier, the transponder preferably being encapsulated so that any contamination of or damage to the transponder is effectively prevented.

In particular when a wide variety of objects are being handled, it is advantageous if the transponder is configured in the form of a mountable or attachable clip or the like, so that transponders with different code data can be associated with the object carrier and thus with the object. It would be possible in this case to work with transponders loaded with predefined code data, in order to assign different program sequences at the respective processing stations to the respective objects.

In light of the teaching of the present invention, it is additionally advantageous if the transponder communicates with at least one receiver, the receiver being understood as an electronic analysis system/control unit. A receiver or corresponding electronic analysis system/control unit can be associated with each excitation coil. It is also possible, when multiple excitation coils are provided, for all of them to communicate with a single receiver. The receiver could in turn comprise a write/read unit so as on the one hand to receive data and on the other hand to transmit data.

In additionally advantageous fashion, the receiver is connected to a process computer and/or an electronic analysis system so that by way of the detected code it is possible not only to recognize the object, but also to activate individual processing steps or processing operations by way of the process computer. The position of the object can be checked or ascertained over the entire course of the processing sequence, and can even be incorporated into the process since the exact position of the object being processed is known.

In principle, it is possible at any time for multiple receivers to be connected to a single process computer and/or to a single electronic analysis system; different receivers can by all means also be connected to different process computers and/or different electronic analysis systems. Individual adaptation to requirements is possible here, and it is certainly conceivable for different processing stations or groups of processing stations also to have different process computers and electronic analysis systems.

It is furthermore possible for the receiver, considered of itself, to have a processing station associated with it, a receiver or even multiple receivers being associated with each processing station.

As already mentioned earlier, the code serves to identify the object carrier and thus the object. It is furthermore possible to use the code, in accordance with the positioning of the particular receiver, for position reporting or position determination of the object carrier and thus of the object. In addition, the code can be used to assign a handling program or processing program, so that specific processing can also be unequivocally assigned to a specific object, unequivocal identification of the object once again being possible after processing.

Lastly, be it noted once again that the object can be a histological or cytological specimen, and the object carrier can be a basket or the like receiving the specimen. Correspondingly, the processing stations could be stations of an automatic stainer for staining histological or cytological specimens, all of the handling and processing of histological and cytological specimens and the corresponding processing stations being controlled and monitored in accordance with the description above, namely by the fact that a unequivocal code can be assigned to the object being processed, on the one hand for identification of the object and on the other hand for assignment of a processing program.

BRIEF DESCRIPTION OF THE DRAWINGS

There are various ways of advantageously embodying and developing the teaching of the present invention. Reference is made, for that purpose, on the one hand to the claims which follow Claim 1, and on the other hand to the explanation below of exemplary embodiments of the invention with reference to the drawings. In conjunction with the explanation of the preferred exemplary embodiments of the invention with reference to the drawings, an explanation is also given of generally preferred embodiments and developments of the teaching. In the drawings:

FIG. 6 shows a further exemplary embodiment of the apparatus according to the present invention concerning an automatic stainer.

DETAILED DESCRIPTION OF THE INVENTION

Figure 1:
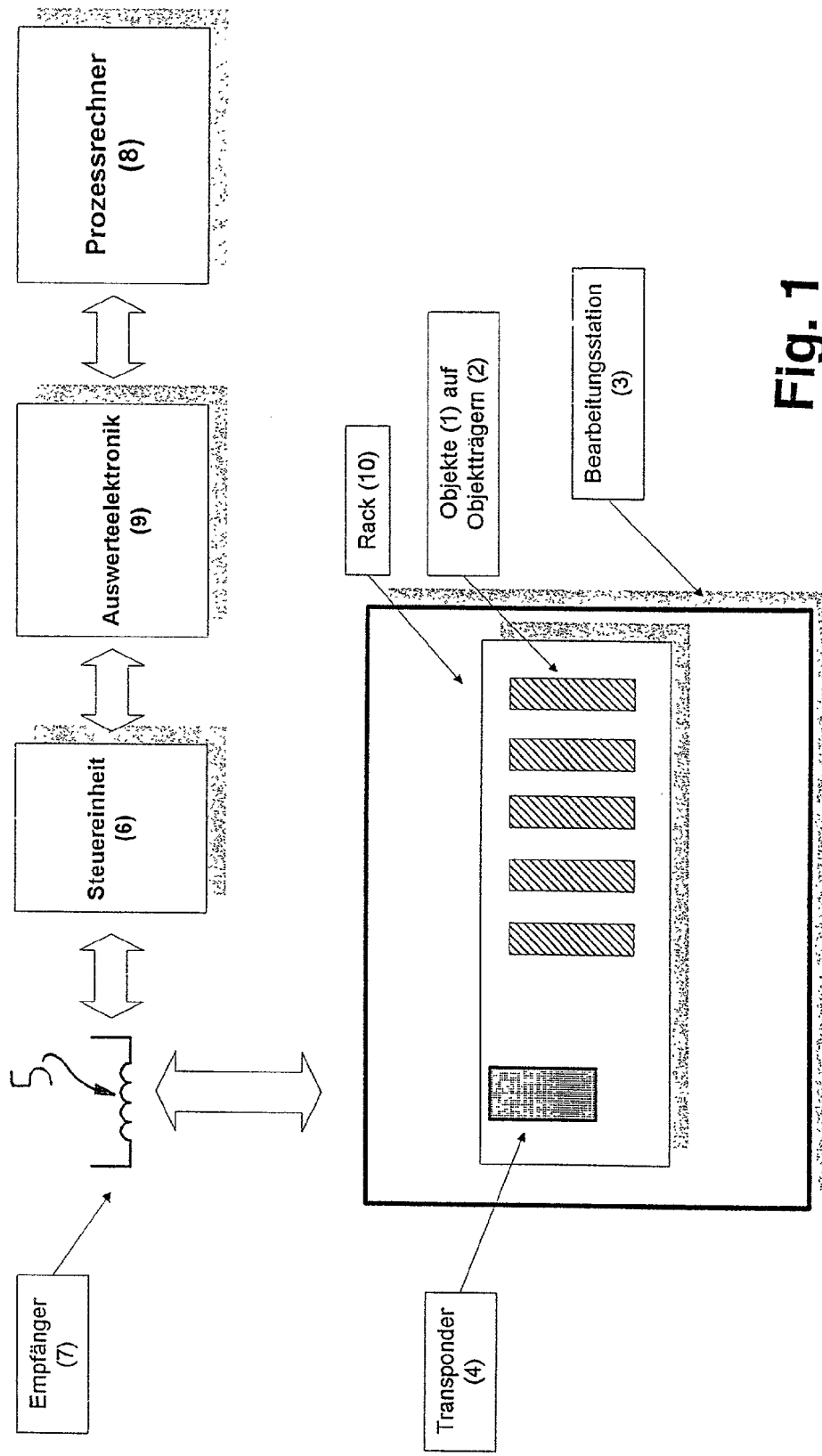
FIG. 1 shows, in a schematic depiction, the general manner of operation of an apparatus according to the present invention.

FIG. 1 shows, in a schematic depiction, the general manner of operation of an apparatus according to the present invention for preferably automatic handling and/or processing of objects 1, the latter being concretely a histological or cytological specimen which is located, for processing, in an object carrier 2 that is merely indicated in FIG. 1. Several of object carriers 2 are arranged in a rack 10.

Figure 3:
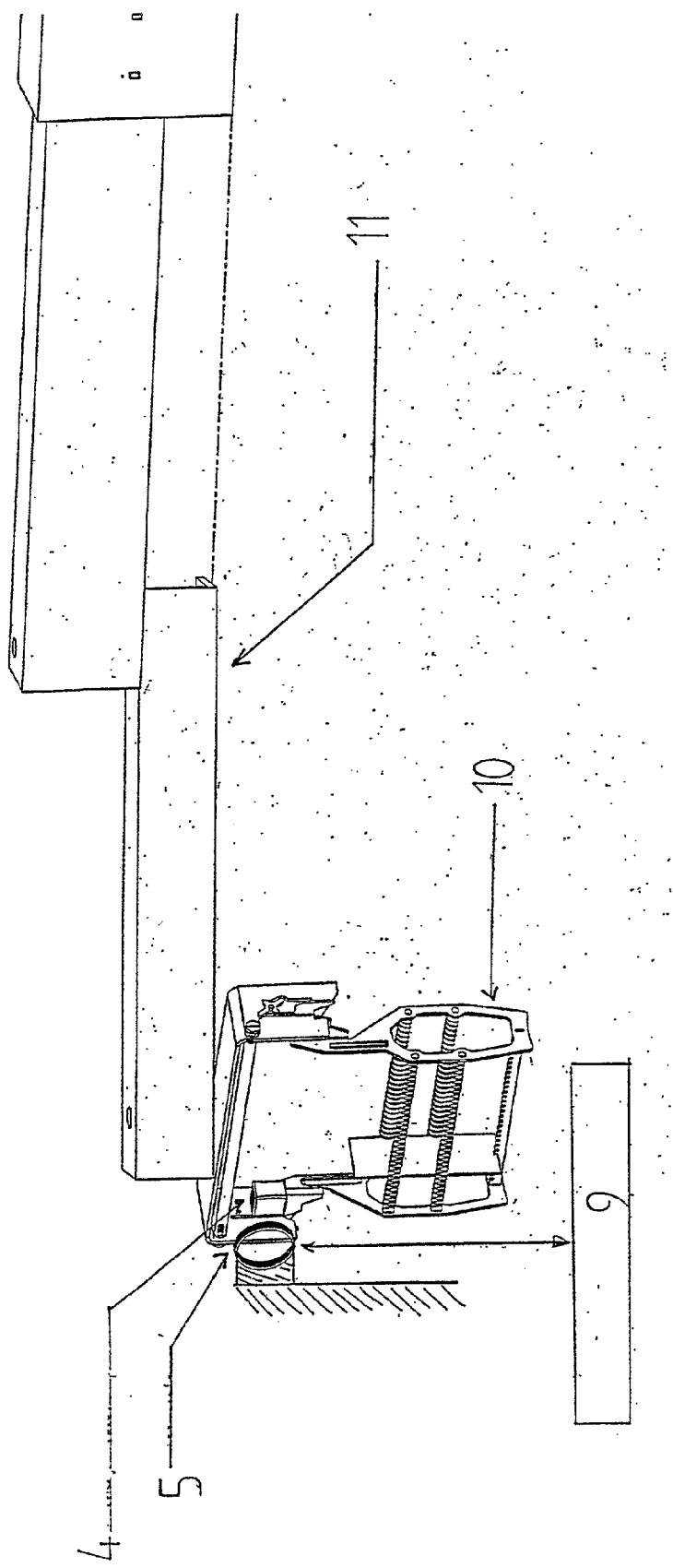
FIG. 3 shows, in a schematic depiction and in part, an exemplary embodiment of an apparatus according to the present invention, an automatic stainer for histological or cytological specimens being shown therein, and the object carrier which bears a transponder being moved therein past an excitation coil at the beginning of the program sequence and thereby identified.

A processing station 3 is also merely indicated in FIG. 3; at processing station 3, on the one hand object 1 or object carrier 2 and/or rack 10 is identified, and on the other hand its presence is ascertained.

According to the present invention, object carrier 2 or rack 10 has a code, and data concerning object 1 and its processing can be assigned to the code. These data can be read or retrieved by way of the code.

Concretely, the code is stored in an electromagnetic storage medium associated with object carrier 2 or rack 10, specifically in a transponder 4 which is to be understood here as a combined transmitter/receiver unit.

FIG. 1 also shows in indicative fashion that an excitation coil 5 for activation of transponder 4 is associated with processing station 3, excitation coil 5 being activatable via a control unit 6.

In the embodiment shown in FIG. 1, transponder 4 is mounted on object carrier 2 or on rack 10. Leaving aside the embodiment in which transponder 4 is mounted directly on object carrier 2, it is also conceivable, for example, for identification to be made not of individual objects but always of collections of objects 1, specifically in so-called racks 10 which contain multiple object carriers 2 or objects 1. Ultimately the histological or cytological specimens (objects 1) are located on object carriers 2; both object carriers 2 and the object carrier holders (i.e. the so-called racks 10) are identified with transponder 4 which is located in the various processing stations 3.

Figure 2:
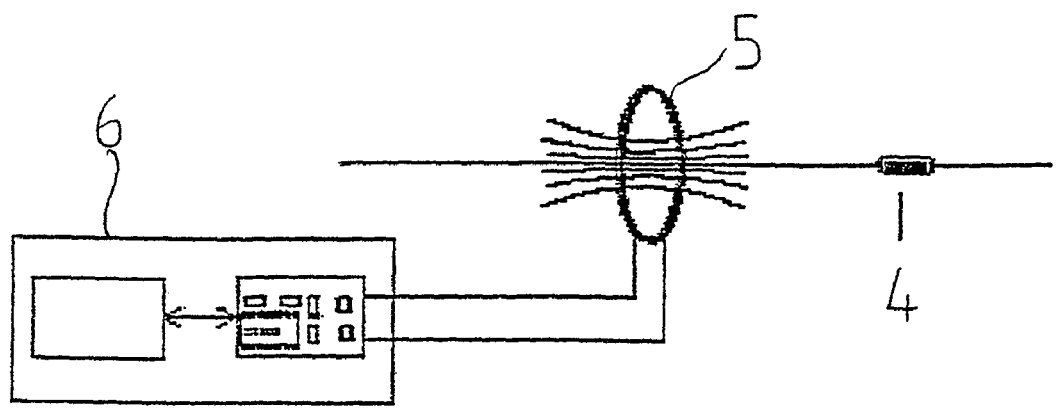
FIG. 2 shows, in a schematic depiction, the general manner of operation of a transponder that can be used in the context of the apparatus according to the present invention as an electronic code medium.

FIG. 2 shows the basic manner of operation of a transponder system, for better comprehension of the teaching of the present invention. Transponder 4 shown therein is embodied as a combined write/read transponder, and in the form of a clip mountable on object carrier 2. In addition, transponder 4 communicates by way of a transmission and reception path with a receiver 7, more precisely with an electronic analysis system/control unit that in turn is connected to a process computer 8 and an electronic control system 9. Although process computer 8 precedes electronic analysis system 9 in the embodiment selected here, it is certainly also possible for electronic analysis system 9 to precede process computer 8. The program sequence can thus be influenced (via process computer 8) by the detection of object 1, the electronic analysis system serving to process the detected data of the respective object 1.

Concerning the depiction in FIG. 2, be it noted with regard to the manner of operation of a transponder system that excitation coil 5 also simultaneously serves as a transmit/receive antenna. Excitation coil 5 generates an excitation field. When an object equipped with a transponder comes into that excitation field, a voltage is induced in a coil provided in the transponder. The transponder thereupon sends a code (a sequence of numbers or digits) to electronic analysis system 9 depicted in FIG. 1. That code is received by the same coil (excitation coil) that generates the excitation field. Excitation coil 5 may thus also simultaneously be referred to as a receive/transmit antenna. The code is processed by the downstream electronic analysis system 9, and associated in a controller or processor with a program in such a way that individual program steps can be activated or influenced.

FIG. 3 shows an exemplary embodiment of an apparatus according to the present invention, here being concretely a partially depicted automatic stainer for staining histological and cytological objects 1 or specimens.

FIG. 3 shows a rack 10 for receiving an object or object carrier; at the beginning of the program sequence, rack 10 is moved by a transport system 11 past excitation coil 5, excitation coil 5 simultaneously also serving as a receive/transmit antenna. Transponder 4 clipped onto rack 10 is activated by excitation coil 5, so that it sends to electronic analysis system 9 the code relevant to object 1 (not shown). It is thereby easily possible to identify object 1 or object carrier 2, or rack 10.

Figure 4:
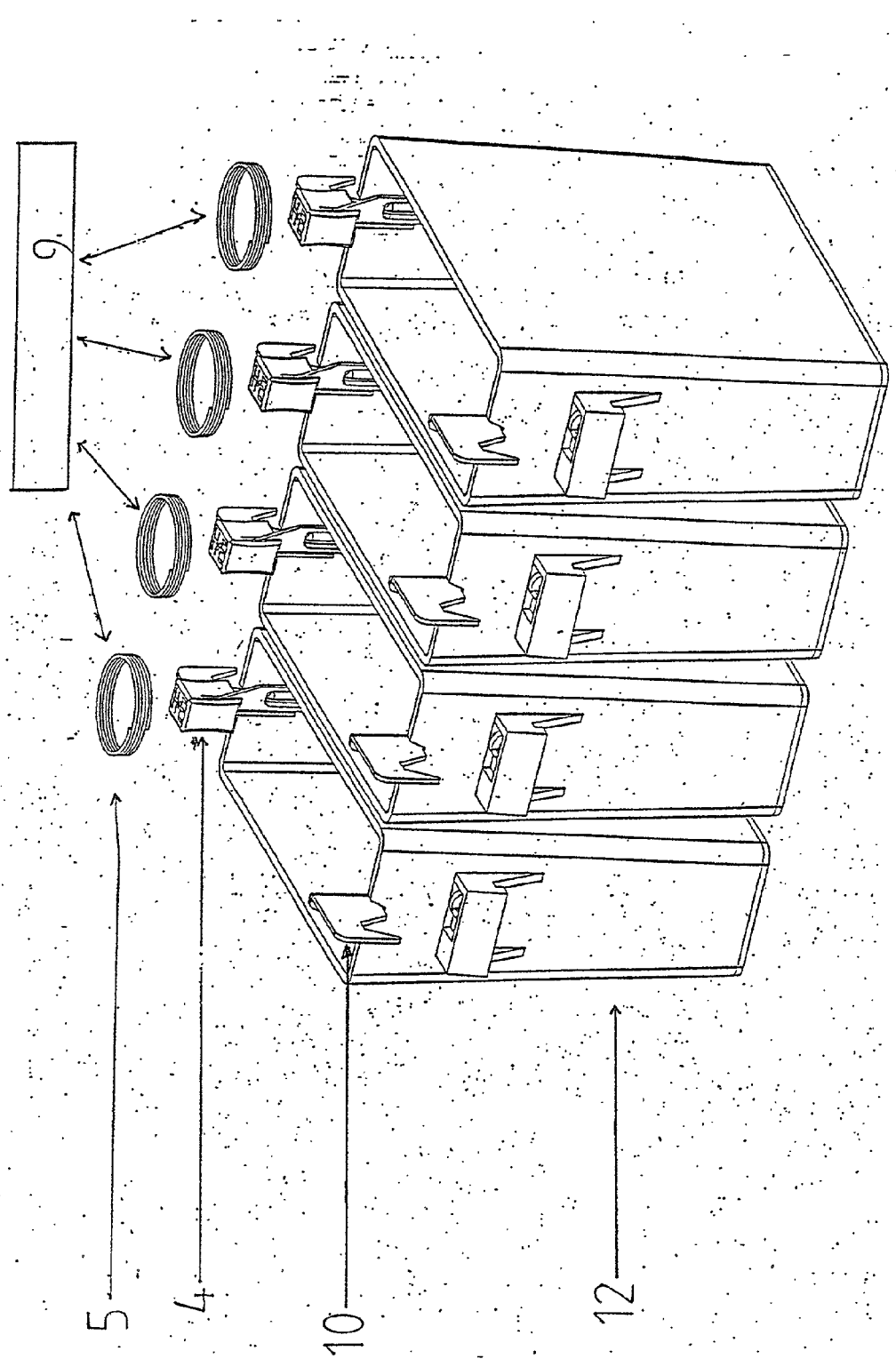
FIG. 4 shows, in a schematic depiction and in part, an exemplary embodiment of an apparatus according to the present invention also concerning an automatic stainer.

FIG. 4 shows the arrangement of a total of four containers 12 of a partially depicted automatic stainer, each container 12 and rack 10 having associated with it a transponder 4 in the form of a transponder clip. A total of four excitation coils 5 serve, at processing stations 3 or at correspondingly defined locations, to activate transponder 4, whereupon the activated transponder 4 forwards the code via excitation coil 5 to electronic analysis system 9.

In the exemplary embodiment shown in FIG. 4, excitation coils 5 are arranged above the respective loading stations. By way of an electronic switchover system, the four excitation coils 5 can be connected successively to an RF module so that racks 10 can be identified by transponders 4 at very short time intervals and assigned to a specific program sequence. Data transfer takes place between transponders 4 and electronic analysis system 9, this being indicated in FIG. 4 by arrows.

Figure 5:
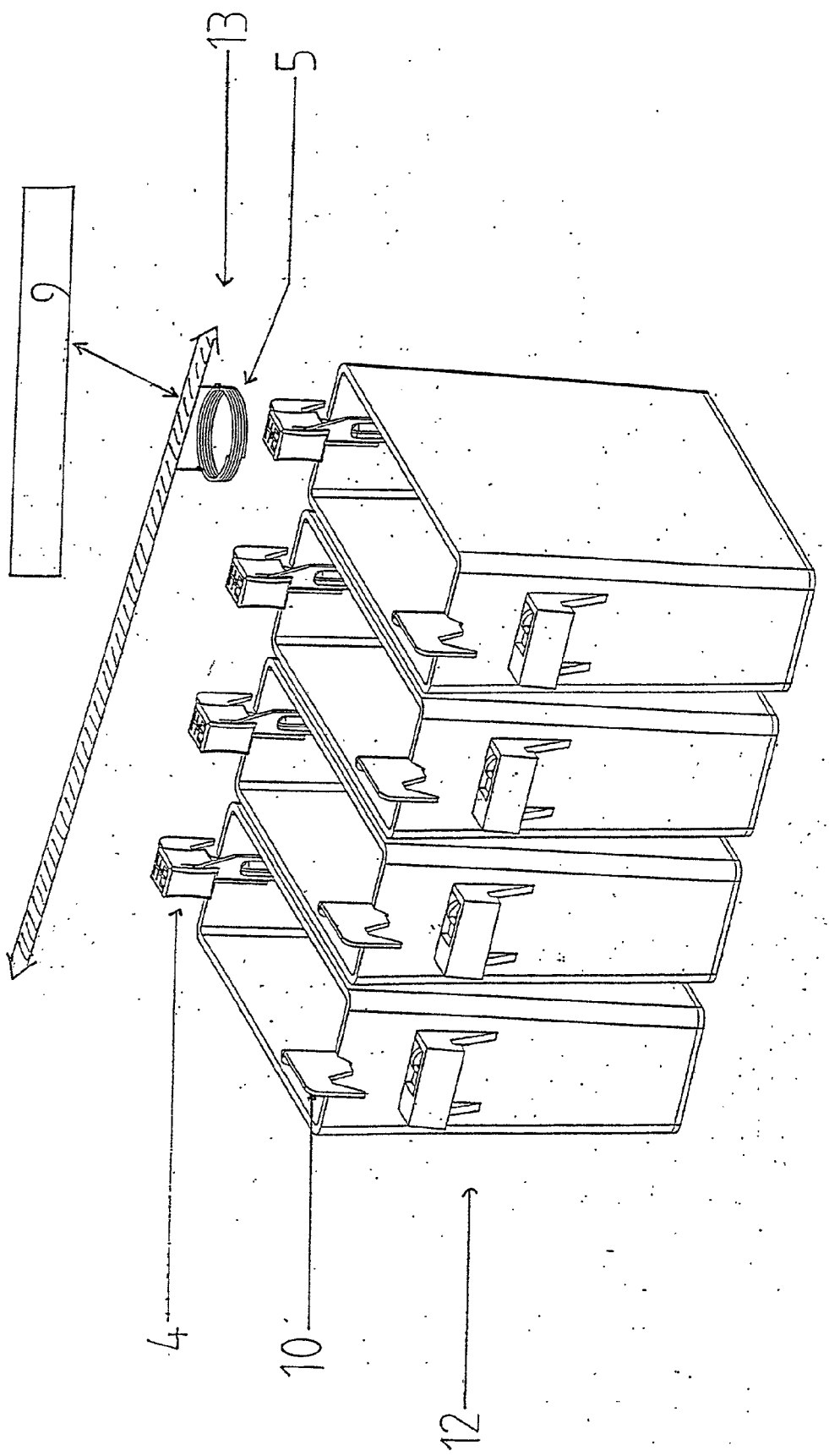
FIG. 5 shows a further exemplary embodiment of an apparatus according to the present invention concerning an automatic stainer.

In the further exemplary embodiment shown in FIG. 5, once again four containers 12 of an automatic stainer are depicted next to one another; here, a single excitation coil 5 is moved past the respective stopping places of the object carriers by way of a special transport system 13 that is merely indicated here. The position of the object carriers or racks 10, and thus the position of the objects, can thus be unequivocally identified. Here as well, transponders 4 communicate with electronic analysis system 9.

Lastly, FIG. 6 shows a further exemplary embodiment of an automatic stainer in which a separate excitation coil 5 and a complete electronic analysis system 9 is provided for each rack 10 that is to be identified. Here again, transponder 4 communicates via excitation coil 5 with electronic analysis system 9, excitation coil 5 simultaneously serving as a receive/transmit antenna.

What is essential in the exemplary embodiment depicted in FIG. 6 is the fact that one excitation coil 5 is associated with each processing station, and in turn a separate electronic analysis system 9 is associated with each excitation coil 5.

In conclusion, be it noted very particularly that the exemplary embodiments discussed above are provided merely for discussion of the teaching claimed, but do not limit it to the exemplary embodiments.

PARTS LIST

1 Object; histological or cytological specimen
2 Object carrier
3 Processing station
4 Transponder
5 Excitation coil; receive/transmit antenna
6 Control unit
7 Receiver
8 Process computer
9 Electronic analysis system
10 Rack
11 Transport system (for rack)
12 Container
13 Transport system (for excitation coil)

What is claimed is:

1. An apparatus for staining histological and/or cytological specimens each mounted on a specimen slide, the apparatus comprising:
　a plurality of processing stations arranged in sequence, each of the plurality of processing stations having an excitation coil associated therewith for generating an excitation field;
　a rack for carrying at least one specimen slide;
　a transponder mounted on the rack for travel with the rack, wherein said transponder is temporarily mounted on the rack by a clip, the transponder having a code associated therewith;
　a transport system for automatically transporting the rack and transponder to and from individual processing stations in the plurality of processing stations; and
　a control unit connected to each of the excitation coils and to the transport system, the control unit executing a processing program to provide commands to the transport system to move the rack and the at least one specimen slide to and from specified processing stations;
　the transponder being activated by the excitation field at a processing station to transmit the code to the control unit, wherein the code is evaluated by the control unit to assign the processing program.

* * * * *